United States Patent
Isaacson et al.

(10) Patent No.: US 10,434,308 B2
(45) Date of Patent: Oct. 8, 2019

(54) IMPEDANCE MATCHING AND ELECTRODE CONDITIONING IN PATIENT INTERFACE SYSTEMS

(71) Applicant: Medtronic, Inc., Minneapolis, MN (US)

(72) Inventors: Benjamin P. Isaacson, Minneapolis, MN (US); Timothy J. Denison, Minneapolis, MN (US); Kunal J. Paralikar, Minneapolis, MN (US); Scott R. Stanslaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 210 days.

(21) Appl. No.: 14/726,028

(22) Filed: May 29, 2015

(65) Prior Publication Data
US 2016/0346534 A1     Dec. 1, 2016

(51) Int. Cl.
*A61B 5/04*     (2006.01)
*A61N 1/08*     (2006.01)
(Continued)

(52) U.S. Cl.
CPC ............ *A61N 1/08* (2013.01); *A61B 5/04001* (2013.01); *A61B 5/0476* (2013.01);
(Continued)

(58) Field of Classification Search
CPC .... A61N 1/08; A61N 1/36185; A61N 1/0529; A61N 1/36067; A61N 1/36135;
(Continued)

(56) References Cited

U.S. PATENT DOCUMENTS

| | | |
|---|---|---|
| 4,525,677 A | 6/1985 | Rorden |
| 4,981,141 A | 1/1991 | Seagalowitz |

(Continued)

FOREIGN PATENT DOCUMENTS

| | | |
|---|---|---|
| WO | 2007058950 A2 | 5/2007 |
| WO | 2013142944 A1 | 10/2013 |

(Continued)

OTHER PUBLICATIONS

International Patent Application No. PCT/US2016/024138, International Search Report and Written Opinion dated May 23, 2016, 13 pages.

(Continued)

*Primary Examiner* — Navin Natnithithadha
*Assistant Examiner* — Andrey Shostak
(74) *Attorney, Agent, or Firm* — Shumaker & Sieffert, P.A.

(57) ABSTRACT

Systems and method may be used for interfacing with a patient. Systems may include a plurality of electrodes in electrical communication with a processor. The processor may determine a relative impedance difference between a first electrode and a second electrode, and apply a sub-therapeutic stimulation pulse to one of the first and second electrodes to adjust the relative impedance difference therebetween. Systems may include a processor capable of one or both of providing therapeutic stimulation to a patient via at least one electrode, and receiving electrical signals indicative of the patient's physiological activity. In some examples, the processor may simultaneously provide therapeutic stimulation to a patient and receive electrical signals from the patient indicative of the patient's physiological activity.

16 Claims, 4 Drawing Sheets

(51) Int. Cl.
*A61B 5/0476* (2006.01)
*A61B 5/00* (2006.01)
*A61N 1/05* (2006.01)
*A61N 1/36* (2006.01)

(52) U.S. Cl.
CPC .......... *A61B 5/6868* (2013.01); *A61N 1/0529* (2013.01); *A61N 1/0534* (2013.01); *A61N 1/36067* (2013.01); *A61N 1/36135* (2013.01); *A61N 1/36185* (2013.01); *A61N 2001/083* (2013.01)

(58) Field of Classification Search
CPC ............ A61N 1/0534; A61N 2001/083; A61B 5/04001; A61B 5/0476; A61B 5/6868
See application file for complete search history.

(56) References Cited

U.S. PATENT DOCUMENTS

| | | | |
|---|---|---|---|
| 5,368,041 A * | 11/1994 | Shambroom | A61B 5/0006 600/544 |
| 5,381,804 A | 1/1995 | Shambroom | |
| 5,776,167 A | 7/1998 | Levine et al. | |
| 6,032,060 A * | 2/2000 | Carim | A61N 1/0472 128/898 |
| 6,463,411 B1 | 10/2002 | Li et al. | |
| 6,493,576 B1 | 12/2002 | Dankwart-Eder | |
| 7,385,443 B1 | 6/2008 | Denison | |
| 7,953,230 B2 | 5/2011 | Nadjar et al. | |
| 8,068,905 B2 | 11/2011 | Freeman et al. | |
| 8,121,694 B2 | 2/2012 | Molnar et al. | |
| 8,248,137 B2 | 8/2012 | Peuscher | |
| 8,260,412 B2 | 9/2012 | Krause et al. | |
| 8,359,083 B2 | 1/2013 | Clark et al. | |
| 8,406,893 B2 | 3/2013 | Krause et al. | |
| 8,428,733 B2 | 4/2013 | Carlson et al. | |
| 8,504,154 B2 | 8/2013 | Wanasek | |
| 8,538,512 B1 | 9/2013 | Bibian et al. | |
| 8,577,457 B2 | 11/2013 | Miller et al. | |
| 8,798,751 B2 | 8/2014 | Spear et al. | |
| 8,849,390 B2 | 9/2014 | Echauz et al. | |
| 8,868,148 B2 | 10/2014 | Engelbrecht et al. | |
| 9,649,492 B2 | 5/2017 | Li et al. | |
| 10,080,898 B2 | 9/2018 | Denison et al. | |
| 2002/0165458 A1 * | 11/2002 | Carter | A61B 5/04286 600/508 |
| 2004/0210148 A1 * | 10/2004 | Van Ess | A61B 5/04286 600/509 |
| 2005/0010265 A1 | 1/2005 | Baru et al. | |
| 2006/0095092 A1 | 5/2006 | Drew | |
| 2008/0132979 A1 | 6/2008 | Gerber | |
| 2008/0243022 A1 | 10/2008 | Donnett et al. | |
| 2009/0045886 A1 | 2/2009 | Gruchalla | |
| 2009/0082691 A1 | 3/2009 | Denison et al. | |
| 2009/0192556 A1 | 7/2009 | Wu et al. | |
| 2010/0010369 A1 | 1/2010 | Pomfrett et al. | |
| 2010/0023084 A1 | 1/2010 | Gunderson | |
| 2010/0100153 A1 * | 4/2010 | Carlson | A61N 1/0529 607/45 |
| 2011/0001497 A1 | 1/2011 | Chetelat et al. | |
| 2011/0040546 A1 | 2/2011 | Gerber et al. | |
| 2011/0125214 A1 | 5/2011 | Goetz et al. | |
| 2011/0201944 A1 | 8/2011 | Higgins et al. | |
| 2011/0257708 A1 | 10/2011 | Kramer et al. | |
| 2012/0065536 A1 * | 3/2012 | Causevic | A61B 5/0476 600/544 |
| 2012/0109258 A1 | 5/2012 | Cinbis et al. | |
| 2012/0194268 A1 | 8/2012 | Chang et al. | |
| 2012/0277820 A1 | 11/2012 | Wu et al. | |
| 2012/0296444 A1 | 11/2012 | Greenberg et al. | |
| 2013/0006324 A1 | 1/2013 | Bradley | |
| 2013/0131755 A1 | 5/2013 | Panken et al. | |
| 2013/0218232 A1 * | 8/2013 | Giftakis | A61N 1/372 607/45 |
| 2013/0328572 A1 * | 12/2013 | Wang | G01R 35/00 324/601 |
| 2014/0277282 A1 * | 9/2014 | Jaax | A61N 1/36139 607/59 |
| 2015/0352085 A1 | 12/2015 | During | |
| 2016/0067497 A1 * | 3/2016 | Levine | A61B 5/6877 607/62 |
| 2016/0346534 A1 | 12/2016 | Isaacson et al. | |

FOREIGN PATENT DOCUMENTS

| | | |
|---|---|---|
| WO | 2014043739 A1 | 3/2014 |
| WO | 2014167418 A2 | 10/2014 |

OTHER PUBLICATIONS

Baker, "A psychophysically derived model of signal combination predicts neural responses in two stimulus domains," Journal of Vision, vol. 14, No. 10, article 1180, Aug. 22, 2014, 1 pp.

"PGA Manual", Multichannel Systems, Nov. 10, 2010, 24 pages.

Goetz et al., "A Novel Model Incorporating Two Variability Sources for Describing Motor Evoked Potentials," Brain Stimulation; May 2, 2014, 12 pages.

Galvan et al., "Long-Term Frequency Tuning of Local Field Potentials in the Auditory Cortex of the Waking Guinea Pig," Journal of the Association for Research in Otolaryngology, May 14, 2001, 17 pages.

U.S. Appl. No. 14/725,998, entitled "Simultaneous Physiological Sensing and Stimulation with Saturation Detection," filed May 29, 2015, 34 pages.

Wang, "Design of a 32-Channel EEG System for Brain Control Interface Applications," Apr. 10, 2012, 10 pages.

Oh et al., Multi-frequency EIT system with radially symmetric architecture: KHU Mark 1, Jun. 26, 2007, 14 pages.

Afshar, "A transnational platform for protyping closed-loop neuromodulation systems," Frontiers in Neural Circuits, vol. 6, Jan. 22, 2013, 15 pp.

Stanslaski, "Design and Validation of a Fully Implantable, Chronic, Closed-Loop Neuromodulation Device with Concurrent Sensing and Stimulation," IEEE, vol. 20, No. 4, Jul. 4, 2012, pp. 410-421.

Goyal, "Automatic gain contro in burst communications systems," RF Design, Feb. 2000, 9 pp.

Response to Communication Pursuant to Rules 161(1) and 162 EPC dated Aug. 8, 2018 from counterpart European Application No. 16714711.5, 11 pp.

Notice of Intent to Grant and Text Intended to Grant from counterpart European Application No. 16714711.5, dated Mar. 20, 2019, 77 pp.

Webster, "Reducing Motion Artifacts and Interference in Biopotential Recording," IEEE Transactions on Biomedical Engineering, vol. BME-31, No. 12, Dec. 1984, pp. 823-826.

Polikov et al., "Response of brain tissue to chronically implanted neural electrodes," Journal of Neuroscience Methods, vol. 148, No. 1, Aug. 8, 2005, 18 pp.

U.S. Appl. No. 16/110,439, entitled "Simultaneous Physiological Sensing and Stimulation With Saturation Detection," filed Aug. 23, 2018, 35 pp.

* cited by examiner

FIG. 4

IMPEDANCE MATCHING AND ELECTRODE CONDITIONING IN PATIENT INTERFACE SYSTEMS

BACKGROUND

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement or other nervous disorders.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. Where electrical stimulation is delivered in the form of electrical pulses, for example, the parameters may include an electrode combination, an amplitude, which may be a current or voltage amplitude, a pulse width, a pulse shape, and a pulse rate.

The sensing and monitoring of electrical signals from the patient's nervous system can be an important aspect of therapeutic and diagnostic procedures. However, such sensing and monitoring presents challenges. Neurological bioelectrical signals have relatively small magnitudes compared to those in other areas of the body, such as cardiac signals, for example. Accordingly, these signals are typically amplified for analysis. However, the application of electrical stimulation obscures these neurological bioelectrical signals during the application of the stimulation. For example, saturation of the amplifiers results, thereby rendering the sensed signal unreliable. As a result, bioelectrical signals are not typically measured during stimulation. Instead, sensing electrodes are often blocked during stimulation and re-enabled after stimulation in an attempt to observe the effect of the stimulation pulse. However, such blocking and re-enabling practice can result in missing useful information that occurs during the stimulation itself.

In addition, sensing signals from the patient's nervous system can be affected by properties of the electrode-tissue interface. For instance, a mismatch in the electrode-tissue interface impedance between a pair of sensing electrodes can lead to limited ability to sense desired electrical signals. Moreover, interface impedances between electrodes and nervous tissue can be unpredictable and therefore cannot be "matched" while placing electrodes in contact with the nerves. Thus, the sensing of electrical signals from a patient's nervous system can be complicated by properties of the electrode-tissue interface.

SUMMARY

Aspects of the present disclosure are directed to systems and methods for interfacing with tissue of a patient. Methods according to some embodiments include measuring a signal indicative of the relative impedance differences between a first electrode and a second electrode that are configured to sense physiological signals of a patient. The measure relative impedance difference may be compared to a predetermine amount. If the impedance difference exceeds the predetermined amount, a sub-therapeutic stimulation pulse may be applied to one of the first and second electrodes to reduce the relative impedance difference between the electrodes. After applying the sub-therapeutic stimulation pulse to reduce the relative impedance difference between electrodes, the method can include measuring an electrical signal between the first and second electrodes indicative of the patient's physiological activity.

Systems according to embodiments of the disclosure can include first and second electrodes configurable to electrically engage tissue of a patient. The system can include a processor in communication with the electrodes configured to receive electrical signals representative of the patient's physiological activity. The processor may additionally or alternatively receive a signal from the first and second electrodes indicative of the relative impedance therebetween. The processor can be configured to provide a stimulation pulse to one of the first and second electrodes to reduce the impedance of that electrode. In some examples, the processor is capable of providing the stimulation pulse to either of the first and second electrodes. The stimulation pulse provided may have at least one non-therapeutic characteristic.

Systems may simultaneously provide therapeutic stimulation pulses to and monitor physiological activity of a patient. Systems can include a plurality of electrodes capable of electrical communication with the patient's tissue and a processor in communication with the plurality of electrodes. The processor can be capable of applying stimulation pulses to one or more of the electrodes and receiving electrical signals from a plurality of the electrodes indicative of physiological signals of the patient. The processor can be configured to determine the relative impedance difference between a first and second of the plurality of electrodes and apply a sub-therapeutic stimulation pules to one of the first and second electrodes to reduce the relative impedance difference. The processor can apply a therapeutic stimulation pulse to a third electrode that is separate from the first and second electrodes and simultaneously receive electrical signals representative of the patient's physiological activity via the first and second electrodes.

DETAILED DESCRIPTION

Figure 1:
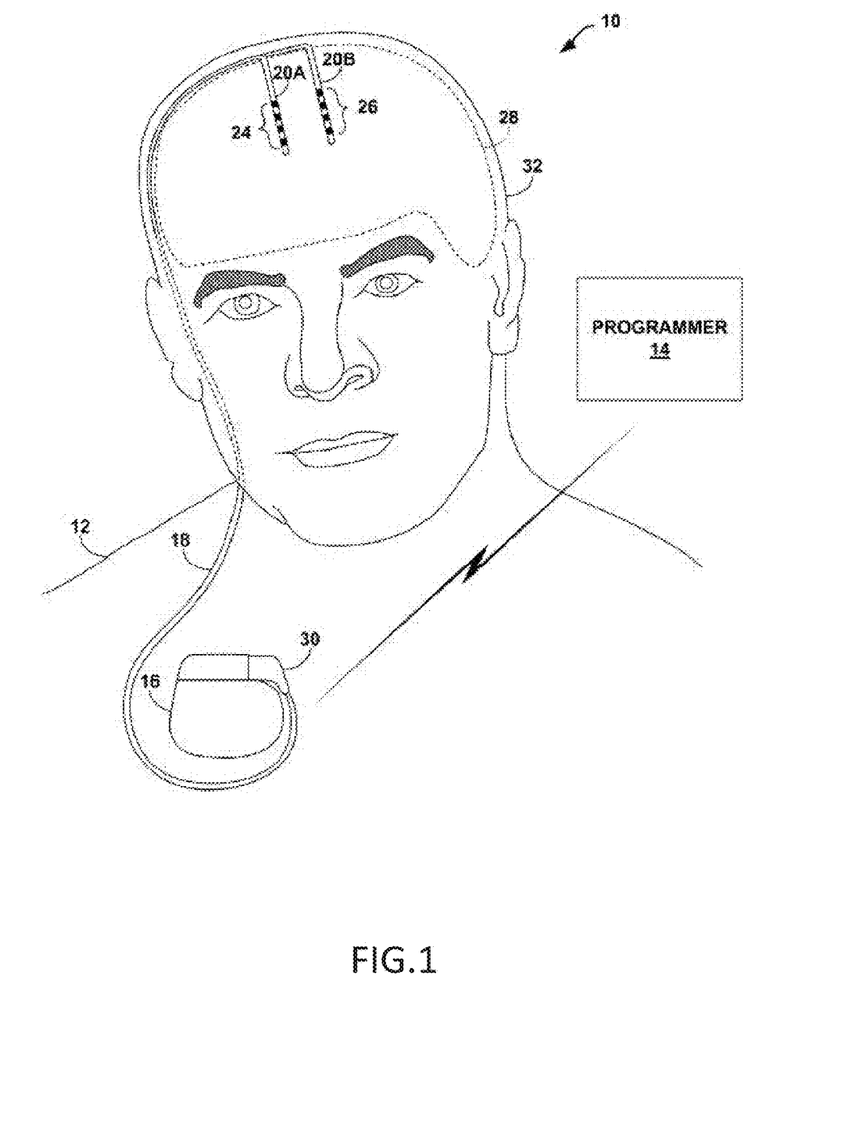
FIG. 1 is a conceptual diagram illustrating an example of a deep brain stimulation (DBS) system.

FIG. 1 is a conceptual diagram illustrating an example nervous interface system 10 that electrically interfaces with the nervous system of a patient. In some examples, the nervous interface system 10 includes a therapy system that delivers therapy to control a patient condition, such as a movement disorder or a neurodegenerative impairment of patient 12. In other examples, the interface system 10 can be used as a diagnostic instrument for receiving electrical signals from the nervous tissue of the patient 12. Patient 12 ordinarily will be a human patient. In some cases, however, therapy system 10 may be applied to other mammalian or non-mammalian non-human patients. While movement disorders and neurodegenerative impairment are primarily referred to herein, in other examples, therapy system 10 may provide therapy to manage symptoms of other patient conditions, such as, but not limited to, seizure disorders or psychological disorders.

A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions. Although movement disorders are primarily referred to throughout the remainder of the application, the therapy systems and methods described herein are also useful for controlling symptoms of other conditions, such as neurodegenerative impairment.

The interface system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B are positioned to interface with a tissue site within brain 28, such as a deep brain site under the dura mater of brain 28 of patient 12. In some examples, electrodes can be configured to interface with one or more regions of brain 28, such as the subthalamic nucleus, globus pallidus or thalamus. Stimulation system can be configured to deliver electrical stimulation to such regions, which may be an effective treatment to manage movement disorders, such as Parkinson's disease. It will be appreciated that in further examples, interface system 10 can be positioned to interface with a nervous tissue site in a region separate from the patient's brain.

In the illustrated embodiment, IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination. It will be appreciated that in other embodiments, such as in an exemplary diagnostic instrument, IMD 16 need not include a therapy module.

The IMD 16 can include a sensing module 46 configured to sense bioelectrical or other electrical signals within the brain 28 via a subset of electrodes 24, 26 of leads 20A and 20B, respectively. While two leads 20A, 20B are shown in the illustrated embodiment, it will be appreciated that embodiments of the invention are not limited to two leads, but may include any appropriate number of leads. For example, various embodiments can include a single lead having a plurality of electrodes or a plurality of leads each having at least one electrode. Generally, each lead of a plurality of leads need not include the same number of electrodes. The subset of electrodes 24, 26 that are used to sense such signals within the brain 28 may be referred to as sense electrodes, a sense electrode combination, or at least one sense electrode. Examples of bioelectrical brain signals include, but are not limited to, electrical signals generated from local field potentials within one or more regions of brain 28, an electroencephalogram (EEG) signal or an electrocorticogram (ECoG) signal.

In stimulation systems, electrical stimulation generated by IMD 16 may be configured to manage a variety of disorders and conditions. In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. In some examples, the stimulation signals can be delivered at or include a stimulation frequency located within a first range of frequencies (e.g., within a first frequency band). As previously indicated, the stimulation electrode combination may indicate the specific electrodes 24, 26 that are selected to deliver stimulation signals to tissue of patient 12 and the respective polarity of the selected electrodes.

In various embodiments, IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory.

Implanted lead extension 18 is coupled to IMD 16 via connector 30. In the example of FIG. 1, lead extension 18 traverses from the implant site of IMD 16 and along the neck of patient 12 to cranium 32 of patient 12 to access brain 28. In the example shown in FIG. 1, leads 20A and 20B (collectively "leads 20") are implanted within the right and left hemispheres, respectively, of patient 12 in order deliver electrical stimulation to one or more regions of brain 28, which may be selected based on the patient condition or disorder controlled by therapy system 10. Other lead 20 and IMD 16 implant sites are contemplated. For example, IMD 16 may be implanted on or within cranium 32, in some examples. Or leads 20 may be implanted within the same hemisphere or IMD 16 may be coupled to a single lead.

Although leads 20 are shown in FIG. 1 as being coupled to a common lead extension 18, in other examples, leads 20 may be coupled to IMD 16 via separate lead extensions or directly to connector 30. In an exemplary stimulating system interfacing with a patient's brain, leads 20 may be positioned to deliver electrical stimulation to one or more target tissue sites within brain 28 to manage patient symptoms associated with a movement disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 or within the cerebral cortex of brain 28 via a burr hole in cranium 32 of patient 12, and electrically coupled to IMD 16 via one or more leads 20.

Example techniques for delivering therapy to manage a movement disorder are described in U.S. Pat. No. 8,121,694, entitled, "THERAPY CONTROL BASED ON A PATIENT MOVEMENT STATE," which was filed on Sep. 25, 2008, which is incorporated herein by reference in its entirety. In some examples described by U.S. patent application Ser. No. 12/237,799 to Molnar et al., a brain signal, such as an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help patient 12 initiate movement or maintain movement, and upon detecting a rest state of patient 12, therapy delivery may be deactivated or otherwise modified.

In the example shown in FIG. 1, electrodes 24, 26 of leads 20 are shown as ring electrodes. Ring electrodes may be used in patient interface applications because they are relatively simple to program and are capable of electrically communicating with any tissue adjacent to electrodes 24, 26. For instance, in a stimulation system interfacing with a patient's brain, ring electrodes are capable of delivering an electrical field to any tissue adjacent to electrodes 24, 26. In other examples, electrodes 24, 26 may have different configurations. For examples, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. As discussed, additionally or alternatively, the system can include a number other than two leads 20, each including more or fewer electrodes than shown.

In this manner, electrical stimulation may be directed to a specific direction from leads 20 to enhance therapy efficacy and reduce possible adverse side effects from stimulating a large volume of tissue. In some examples, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12.

In general, the subsets of electrodes 24, 26 that are used as stimulation electrodes and as sense electrodes can be selected by a variety of selection processes, some of which are described in the commonly-assigned U.S. Pat. No. 8,428,733 to Carlson et al., entitled, "STIMULATION ELECTRODE SELECTION," which was filed on Sep. 21, 2009 and is incorporated herein by reference in its entirety. In some embodiments, any electrodes 24, 26 or electrode combinations are capable of providing electrical signals to and receiving signals from the brain 28 or other nervous tissue of the patient. In other embodiments, such as diagnostic systems, electrodes 24, 26 or electrode combinations can be capable of receiving signals from proximate nervous tissue of the patient.

External programmer 14 wirelessly communicates with IMD 16 as needed to provide or retrieve therapy or diagnostic information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate through the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

In therapeutic stimulation systems, the clinician may also store therapy programs within IMD 16 with the aid of programmer 14. During a programming session, the clinician may determine one or more therapy programs that may provide efficacious therapy to patient 12 to address symptoms associated with a patient condition, such as a movement disorder. In some examples, the programs may deliver stimulation in a closed-loop manner, such as in response to one or more different patient states, such as a sleep state, movement state or rest state. For example, in stimulation systems, the clinician may select one or more stimulation electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., muscle activity or muscle tone).

Programmer 14 may assist the clinician in the creation/ identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or BLUETOOTH specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

In some examples, a therapy system may be implemented to provide chronic stimulation therapy to patient 12 over the course of several months or years. However, a therapy system may also be employed on a trial basis to evaluate therapy before committing to full implantation. If implemented temporarily, some components of stimulation system may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates the stimulation system provides effective treatment to patient 12, the clinician may implant a chronic stimulator within patient 12 for relatively long-term treatment.

In other examples, an interface system 10 may be implemented for diagnostic or monitoring purposes over a period of time. A temporary system may be used for a patient undergoing a one-time diagnostic procedure. However, if a patient will require repeated or periodic monitoring, a purely diagnostic system 10 may be implanted. In some further examples, an implanted system for diagnostic purposes may be reprogrammed, for example, by programmer 14, to enable a stimulation program to operate via the implanted system.

Figure 2:
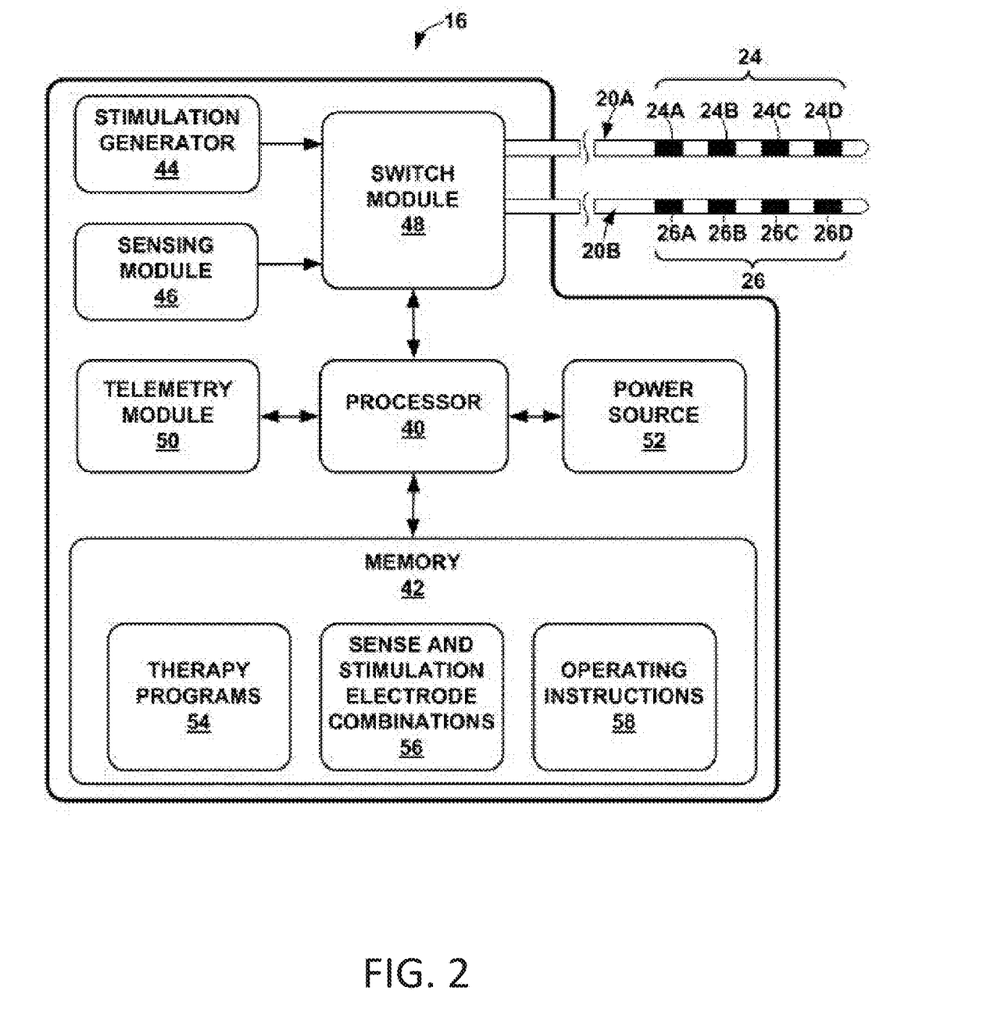
FIG. 2 is a functional block diagram illustrating components of an example medical device.

FIG. 2 is a functional block diagram illustrating components of an example IMD 16 for a stimulating system. In the example shown in FIG. 2, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

As previously discussed, in the example shown in FIG. 2, memory 42 stores therapy programs 54, sense electrode combinations and associated stimulation electrode combinations 56, and operating instructions 58 in separate memories within memory 42 or separate areas within memory 42. In addition, in some examples, memory 42 may store a bioelectrical brain signal sensed via at least some of the stored sense electrode combinations and/or one or more frequency band characteristics of the bioelectrical brain signals. Each stored therapy program 52 defines a particular program of therapy in terms of respective values for electrical stimulation parameters, such as a stimulation electrode combination, electrode polarity, current or voltage amplitude, pulse width, and pulse rate. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 56 stores sense electrode combinations and associated stimulation electrode combinations. As described above, in some examples, the sense and stimulation electrode combinations may include the same subset of electrodes 24, 26, or may include different subsets of electrodes. Stimulation may be delivered in a bi-polar manner between two or more electrodes 24, 26 on leads 20, or may instead be delivered in a unipolar manner between an electrode on leads 20 and a common reference point. In some examples, the housing (or "can") of IMD 16 can function as a common reference. Similarly, sensing may be performed in a bi-polar manner between two electrodes 24, 26 on leads 20, or in a unipolar manner between an electrode 24, 26 on leads 20 and a common reference point such as the housing of IMD 16. Operating instructions 58 guide general operation of IMD 16 under control of processor 40, and may include instructions for measuring the impedance of electrodes 24, 26 and/or determining the distance between electrodes 24, 26.

Stimulation generator 44, under the control of processor 40, generates stimulation signals for delivery to patient 12 via selected combinations of electrodes 24, 26. An example range of electrical stimulation parameters believed to be effective in DBS to manage a movement disorder of patient include:

1. Frequency: the stimulation frequency can be a within a first range of frequencies, for example, between approximately 100 Hz to approximately 500 Hz, between approximately 120 Hz and approximately 200 Hz. In some examples, the stimulation frequency can be applied at approximately 130 Hz.

2. Voltage Amplitude: between approximately 0.1 volts and approximately 50 volts, such as between approximately 0.5 volts and approximately 20 volts, or approximately 5 volts.

3. Current Amplitude: A current amplitude may be defined as the biological load in which the voltage is delivered. In a current-controlled system, the current amplitude, assuming a lower level impedance of approximately 500 ohms, may be between approximately 0.2 milliamps to approximately 100 milliamps, such as between approximately 1 milliamps and approximately 40 milliamps, or approximately 10 milliamps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 44 generates electrical stimulation signals in accordance with the electrical stimulation parameters noted above. Other ranges of therapy parameter values may also be useful, and may depend on the target stimulation site within patient 12, which may or may not be within brain 28. While stimulation pulses are described, stimulation signals may be of any form, such as continuous-time signals (e.g., sine waves) or the like. In general, a stimulation signal may include any arbitrarily shaped waveform. In some examples, the efficacy of the stimulation waveform may be dependent on the location in the patient's body, the contact with the patient's nervous tissue, or other factors. In some embodiments, the waveform of the stimulation signal may be selected based on particular factors of a patient.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40 herein may be embodied as firmware, hardware, software or any combination thereof. Processor 40 controls stimulation generator 44 according to therapy programs 52 stored in memory 42 to apply particular stimulation parameter values specified by one or more of programs, such as amplitude, pulse width, and pulse rate. In general, as used herein, the processor may be configured to perform actions such as providing or receiving signals, pulses, and the like. In various embodiments, the processor 40 is capable of performing such functions directly. Additionally or alternatively, the processor 40 may perform such actions indirectly by causing another component, such as stimulation generator 44 or the like, to perform such functions. In some examples, the processor is configured to perform such actions based in instructions located in memory 42. Additionally or alternatively, processor 40 may include internal or dedicated memory separate from memory 42.

In the example shown in FIG. 2, the set of electrodes 24 includes electrodes 24A, 24B, 24C, and 24D, and the set of electrodes 26 includes electrodes 26A, 26B, 26C, and 26D. In some embodiments, adjacent electrodes (e.g., 24A, 24B) are separated by at least 1 millimeter (mm), and in some embodiments, at least 1.5 mm. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48. As described, in some examples, IMD 16 does not include stimulation generator 44, and is configured for monitoring and diagnostic purposes.

Stimulation generator 44 may be a single channel or multi-channel stimulation generator. In particular, stimulation generator 44 may be capable of delivering, a single stimulation pulse, multiple stimulation pulses or continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Sensing module 46, under the control of processor 40, may sense bioelectrical brain signals and provide the sensed bioelectrical brain signals to processor 40. Processor 40 may control switch module 48 to couple sensing module 46 to a selected combinations of electrodes 24, 26, i.e., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal sensed across the selected electrodes 24, 26 to sensing module 46. The bioelectrical brain signal may include electrical signals that are indicative of electrical activity within brain 28 of patient 12.

Although sensing module 46 is incorporated into a common housing with stimulation generator 44 and processor 40 in FIG. 2, in other examples, sensing module 46 may be in a separate housing from IMD 16 and may communicate with processor 40 via wired or wireless communication techniques. Example bioelectrical brain signals include, but are not limited to, a signal generated from local field potentials within one or more regions of brain 28. EEG and ECoG signals are examples of local field potentials that may be measured within brain 28. However, local field potentials may include a broader genus of electrical signals within brain 28 of patient 12.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

In some instances, sense signals received by the sensing module 46 can include signals of interest within a second range of frequencies that is separate from the first range of frequencies of the stimulation signal. In some embodiments, the signals of interest in the sense signals can include signals within the beta band. The beta band may include a frequency range of about 10 Hertz (Hz) to about 35 Hz, such as about 10 Hz to about 30 Hz or 13 Hz to about 30 Hz. Other signals of interest can include additional or alternative frequency bands, such as delta (e.g., less than approximately 4 Hz), theta (e.g., between approximately 4 Hz and approximately 8 Hz), alpha (e.g., between approximately 8 Hz and approximately 13 Hz), gamma (e.g., between approximately 35 Hz and approximately 100 Hz), or other known neurological frequency bands. In some examples, signals of interest are not limited to any one neurological frequency band, but can more generally be contained within a second frequency band which includes a range of frequencies overlapping with at least one neurological frequency band.

Signals of interest can include a variety of frequency bands according to the patient and the patient's condition. For instance, for certain patients (e.g., patients with Parkinson's disease), signals in the beta frequency band can be of particular interest to a clinician or physician observing the sense signals. However, neural signals can have a relatively low magnitude, for example in the microvolt (µV) range, and as a result can be difficult to analyze. Accordingly, in some examples, the sensing module 46 can include a signal chain comprising a variety of components for processing the signals received from one or more sensing electrodes or sense electrode combinations. For example, the sensing module 46 can include one or more pre-amplifiers, amplifiers, filters, analog-to-digital converters (ADC's), and the like. Such components can assist in the analysis of the sensed signals of interest by improving or maximizing the fidelity of the sensed signals.

As described previously, stimulation pulses can be applied to a patient's brain or other tissue at a stimulation frequency within a first range of frequencies. According to various therapy parameters, various properties of stimulation pulses may include select electrode combination and polarity, pulse amplitude, pulse width, duty cycle, and frequency. In various treatment programs, stimulation pulses are intended to affect the bioelectrical signals in the patient, such as to suppress or promote such signals. For example, a stimulation signal can be applied to the patient's brain via at least one stimulation electrode (e.g., a unipolar stimulation electrode, a bi-polar stimulation electrode combination, etc.) in order to achieve some therapeutic benefit that may be reflected by a change in bioelectrical signals in one or more frequency bands. Additionally or alternatively, a stimulation signal can be applied to a first anatomical target of a patient's nervous system to affect bioelectrical signals in a second anatomical target of the patient's nervous system. Accordingly, it can be advantageous to monitor the bioelectrical signals within the patient's brain or other nervous tissue while simultaneously applying a stimulation signal in order to observe the effect of one on the other. That is, sensing the sense signal from at least one sensing electrode while simultaneously applying a stimulation signal via at least one stimulation electrode can provide real time feedback of the efficacy of the applied stimulation signal. In addition, simultaneously monitoring sense signals while applying stimulation signals can provide information regarding the level of stimulation required for effective promotion or suppression of signals of interest as well as indicate potential side effects of the stimulation on the patient.

In some cases, the one or more stimulation frequencies are selected to be outside of the frequency band of interest for sensing so that stimulation artifacts are not present, or are minimized, in the sensed signal. For instance, in some examples, the first range of frequencies does not overlap with the second range of frequencies. This can be done in order to limit interference between the stimulation signal and sensed signals of interest. By analyzing the frequency content of the resulting sense signal, signals of interest in the second range of frequencies can be analyzed independently from artifacts from the stimulation signal in the first range of frequencies. In other instances, the first and second frequency ranges may overlap, in which stimulation signals may have similar frequency content as signals of interest.

As discussed, in some instances, the magnitude of signals of interest in the second range of frequencies can be relatively small. The sense signal can be processed to create a processed signal, which can facilitate analysis of the signals of interest. For example, the sensing module 46 can include at least one amplifier for amplifying the received sense signal. In various embodiments, the at least one amplifier can be configured to amplify any portion of the sense signal. For example, the at least one amplifier can amplify the entire received sense signal or only certain frequencies of the received sense signal. In some examples, amplification of the sense signal is a function of frequency of the received sense signal. In further examples, frequencies within the second range of frequencies are amplified more than the frequencies in the first range of frequencies.

Amplification of the sense signal can lead to increased ability to analyze the efficacy of the stimulation signal on the patient. However, excessive amplification can result in the obscuring of data, rendering the amplified sense signal unreliable. For example, if the amplification of the sense signal is too high, the signal chain can become saturated, resulting in a potentially misleading processed signal. In some instances, when saturation occurs, the processed signal might indicate that the signals of interest are responding to stimulation as desired when in reality the observed change in the processed signal is an artifact of the saturation and the patient is not actually receiving adequate treatment. In other instances, saturation may result in disguised changes in the signals of interest, leading to a misrepresentation that the patient is not receiving adequate treatment. To compensate for some such instances, aspects of the stimulation signal may be unnecessarily adjusted beyond a desired magnitude in order to achieve observable changes in the signals of interest. In general, saturation can lead to a variety of undesirable circumstances, such as a lack of therapy provided to a patient, an abundance of unnecessary therapy provided to the patient, which can drain the power source unnecessarily or lead to side effects in the patient, or a generally unusable signal from which a conclusion cannot be reached.

In some examples, saturation occurs when artifacts from the stimulation signal in the received sense signal are too large, resulting in saturation when the signal is amplified. In some instances, sufficient amplification of the sense signal in order to observe signals of interest can result in saturation due to amplified artifacts from the stimulation signal when simultaneously sensing and stimulating. In particular, the likelihood of such a saturation event can increase due to a low common-mode rejection ratio (CMRR) between electrodes in a sense electrode combination. That is, in some examples, a sense electrode combination proximate at least one stimulation electrode receives bioelectrical signals from the patient's nervous tissue. Artifacts from the stimulation signal also appear on each electrode in the sense electrode combination (thus, in the common mode). If the CMRR is too low, these artifacts will not be reduced from the resulting sense signal, which can lead to saturation.

In some instances, a low CMRR can be due to an impedance mismatch between the electrodes of a sense electrode combination. In some cases, even if electrodes 24, 26 are identical and have matching impedances when isolated from the patient, the electrode-tissue interface of implanted electrodes contributes to the overall impedance, and can vary widely from electrode to electrode. It is this total impedance mismatch that can lead to a low CMRR. An improved impedance match, and accordingly an improved CMRR, can reduce artifacts from the stimulation signal in the sense signal, allowing for a higher gain to be used when amplifying the sense signal.

Application of an electrical stimulation pulse via an electrode in place in a patient's nervous tissue can effectively lower and also stabilize the electrode-tissue impedance associated with that electrode. This general concept is referred to as "conditioning" the electrode(s). Effective stimulation pulses for reducing the electrode-tissue interface impedance are preferably sub-therapeutic, so that they do not have a therapeutic effect on the patient and therefore would not affect the therapeutic treatment plan for the patient.

In general, sub-therapeutic pulses can be pulses having at least one non-therapeutic characteristic contributing to it not having a therapeutic effect on the patient. Such characteristics may include any combination of the magnitude, frequency, duration, shape, or other pulse characteristics that can affect the therapeutic efficacy of the pulses. Accordingly, in therapeutic stimulation systems, therapeutic stimulation pulses may differ from electrode conditioning pulses in one or more characteristics affecting the efficacy of the pulse for therapeutic purposes.

In addition, the conditioning effect of the application of a stimulation pulse is a localized phenomenon, generally extending on the order of hundreds of microns ($\mu$m), which is typically significantly less than the distance between nearest electrodes. Accordingly, stimulation pulses can be applied to at least one electrode 24, 26 in order to adjust the total impedance at only that electrode.

Various embodiments of the nervous interface system include a plurality of electrodes 24, 26 for applying stimulation to and sensing bioelectrical signals from a patient's nervous tissue. The IMD 16 can generally control which electrodes 24, 26 are utilized for stimulation and sensing. In some embodiments, the IMD 16 can cause stimulation of any appropriate magnitude to be applied from any electrodes, for example, via stimulation generator 44. Additional or alternatively, the IMD 16 can receive signals from any of the electrodes, for example, via sensing module 46. As described in U.S. Pat. No. 8,428,733, which is incorporated by reference herein, various programs can be employed to determine which electrodes are used to perform such functions. In some examples, a stimulation electrode (or stimulation electrode combination) is selected based on its efficacy for providing therapy to the patient. When a stimulation electrode is determined, the optimal sensing electrode (or sense electrode combination) can be based on proximity to the stimulation electrode in order to sense bioelectrical signals affected by the stimulation signal. Thus, in some embodiments, the IMD 16 can generally designate at least one stimulation electrode and at least one associated sense electrode for use during stimulation therapy from a plurality of electrodes 24, 26 in the patient's brain.

In some embodiments, the IMD 16 can perform impedance analysis on at least one electrode 24, 26. Accordingly, in some embodiments, the system can be configured to monitor the relative impedance difference between a pair of electrodes, such as a sense electrode combination. The system can monitor a relative impedance difference between electrodes in a number of ways. In some instances, as described above, the IMD 16 can perform impedance measurements to determine the impedance of each electrode. Such individual electrode impedance measurements may be performed as unipolar impedance measurements in which, for example, the impedance between each electrode 24, 26 and a common reference point is determined. In various examples, the common reference point can be a designated electrode on a lead or a housing of a system component, such as the IMD 16. In such instances, relative impedance differences can be determined from the measured impedances, for example, by subtracting one unipolar impedance measurement from the other. In some such embodiments, the electrode having a higher electrode-tissue interface impedance of a par of electrodes can be determined.

In other examples, the system can apply an identifiable stimulation pulse to the patient's nervous tissue proximate a sense electrode combination, observe the resulting signal on the sense electrode combination, for example, in a bi-polar manner between two of the lead electrodes 24, 26, and determine the CMRR of the sense electrode combination. The determined CMRR can be used to indicate the relative impedance difference between the electrodes in the sense electrode combination. For example, in some embodiments, the system can associate the CMRR between two electrodes with a relative impedance difference between those two electrodes. In some examples, associating the CMRR between electrodes with the relative impedance difference therebetween can be performed using a lookup table or an equation stored in memory 42. Other appropriate methods for determining the relative impedance difference between a pair of electrodes may also be used.

If the determined relative impedance difference between sensing electrodes is sufficiently high (e.g., greater than a 10% mismatch, greater than a 20% mismatch, etc.), a stimulation pulse can be applied to one of the electrodes in order to reduce the impedance of that electrode and the relative impedance difference between the electrodes in the sense electrode combination. For example, if a first electrode in a sense electrode combination exhibits higher impedance than a second electrode, sub-therapeutic stimulation can be applied to the first electrode in order to reduce its impedance, and thus the relative impedance difference between the electrodes. In other examples, such as in some bipolar configuration CMRR measurements, it may not be known which of the first and second electrodes exhibits the higher impedance. In some such embodiments, the sub-therapeutic stimulation can be applied to one of the electrodes (e.g., the first electrode) and the relative impedance difference can be observed. If the relative impedance difference increased, subsequent sub-therapeutic stimulation can be applied to the other electrode (e.g., the second electrode). Conversely, if the relative impedance difference decreased, the sub-therapeutic stimulation can be continued to be applied to the same electrode (e.g., the first electrode) until the impedance difference is at an acceptable level.

In some embodiments, the system can include a closed-loop feedback to determine when sufficient electrode conditioning has been applied. In some examples, the system can analyze the relative impedance difference between electrodes in a sense electrode combination and determine if conditioning of one of the electrodes is desirable. In some cases, determining if conditioning of one of the electrodes is desirable comprises comparing the determined relative impedance difference to a threshold, such as a 10% difference or a 20% difference in impedance. If the relative impedance difference exceeds the threshold, then conditioning is considered to be desirable.

The system can apply electrode conditioning to one of the electrodes of the sense electrode combination in order to reduce the relative impedance difference between them. In some examples, the system can alternatingly apply a sub-therapeutic stimulation to one of the electrodes to condition the electrode, stop conditioning the electrode, determine the relative impedance difference between the electrodes, and, in the event that that relative impedance difference exceeds a predetermined threshold, resume conditioning the electrode. Such steps can be repeated until the determined relative impedance difference no longer exceeds the predetermined threshold. Additionally or alternatively, the system can simultaneously determine the relative impedance difference between the electrodes and provide the sub-therapeutic stimulation to one of the electrodes, and monitor the relative impedance difference in real time while continuing to apply the sub-therapeutic stimulation until the relative impedance difference decreases below the predetermined threshold.

It will be appreciated that a variety of processes as described herein can be performed manually, for example, via a programmer 14 interfacing with IMD 16; or automatically, for example, via programs stored in memory 42 and executable by processor 40 of the IMD. In some instances, the system can automatically initiate such processes by performing one or more steps in the process (e.g., determining a relative impedance difference between electrodes or applying sub-therapeutic stimulation to an electrode in a conditioning step), by alerting a user to perform one or more steps in the process, or a combination of the two. In general, the system can initiation relative impedance difference analysis and electrode conditioning based on a variety of factors.

In some instances, a system can be configured to determine the relative impedance difference between electrodes prior to the execution of a scheduled event, such as a scheduled monitoring of a patient's bioelectrical signals or providing therapeutic stimulation to a patient. That is, if a patient is scheduled to undergo a certain procedure at a scheduled time, the system may automatically determine the relative impedance difference between electrodes in advance of the scheduled procedure so that any desired electrode conditioning can be performed prior to the scheduled procedure. In some such embodiments, memory 42 can be programmed with the patient's appointment or treatment schedule so that appropriate conditioning can be performed prior to the scheduled appointment or treatment. In various examples, the conditioning may be initiated automatically, by a clinician, or even by the patient via the programmer 14. In embodiments in which the patient receives chronic therapy based on programs stored in memory 42, the system can perform any impedance monitoring and conditioning automatically prior to scheduled therapy.

In some instances, the system can initiate relative impedance difference analysis and, if desirable, electrode conditioning, based on the onset of a detected event. For example, if the system or another medical system in communication with the programmer 14 or IMD 16 detects the onset of an event of interest outside of a scheduled procedure, the system can initiate a relative impedance analysis to determine if electrode conditioning is desirable, and, if so, perform an electrode conditioning operation. In various embodiments, the amount of electrode conditioning performed is dependent on the detected event of interest. For example, in some instances, responding to the event of interest with a therapeutic stimulation pulse from at least one stimulating electrode and receiving senses signals via at least one sense electrode is given priority over electrode conditioning. In other instances, the system permits a limited amount of time for performing electrode conditioning before ceasing conditioning and performing an alternative procedure.

In some instances, once the system determines that the relative impedance difference between electrodes is below a predetermined threshold, the system will automatically initiate a future impedance observation, and, if necessary, electrode conditioning after a certain amount of time. The amount of time before initiating future impedance analysis and possible electrode conditioning can be a predefined constant, or otherwise based on the last determine relative impedance difference, user input, or any other system parameter. Initiating the impedance monitoring and conditioning can include automatically performing such processes, or prompting a user, such as a patient or clinician, to perform the process.

In some instances, the system is configured to initiate relative impedance difference analysis based on a detected saturation event. That is, in some embodiments, the system (e.g., IMD 16) is configured to detect saturation (e.g., of at least one component of the signal chain) as described, for example, in patent application Ser. No. 14/725,998 entitled "SIMULTANEOUS PHYSIOLOGICAL SENSING AND STIMULATION WITH SATURATION DETECTION," filed May 29, 2015, which is incorporated herein by reference in its entirety. As described, signal chain saturation can be a result of an insufficient CMRR of a sense electrode combination. Accordingly, the system can initiate an electrode conditioning process based on a determined relative impedance difference between electrodes in order to improve the CMRR of the electrodes and eliminate saturation.

It will be appreciated that, while often described herein as being based on the determination of a relative impedance difference, a system or system operator can perform an electrode conditioning procedure without first determining a relative impedance difference. For example, in the event of detected saturation, a system may omit the step of determining the relative impedance difference between the electrodes and automatically perform an electrode conditioning procedure in order to improve the CMRR of the sense electrodes receiving the sense signal.

In some systems, the longer electrodes are inactive and in contact with the patient's brain tissue, the more difficult it becomes to adjust the impedance of the electrode-tissue interface by stimulation. Accordingly, in some embodiments, the system is configured to periodically perform electrode conditioning whether or not the relative impedance difference between electrodes in a sense electrode combination is greater than a predetermined threshold in order to maintain the pliability of the electrode impedance. Additionally or alternatively, the system can provide a user interface via the programmer 14 by which a user can manually initiate electrode conditioning. In some such embodiments, the system can be configured to automatically perform such regular conditioning procedures periodically or to indicate to a user to manually perform an electrode conditioning procedure.

Figure 3:
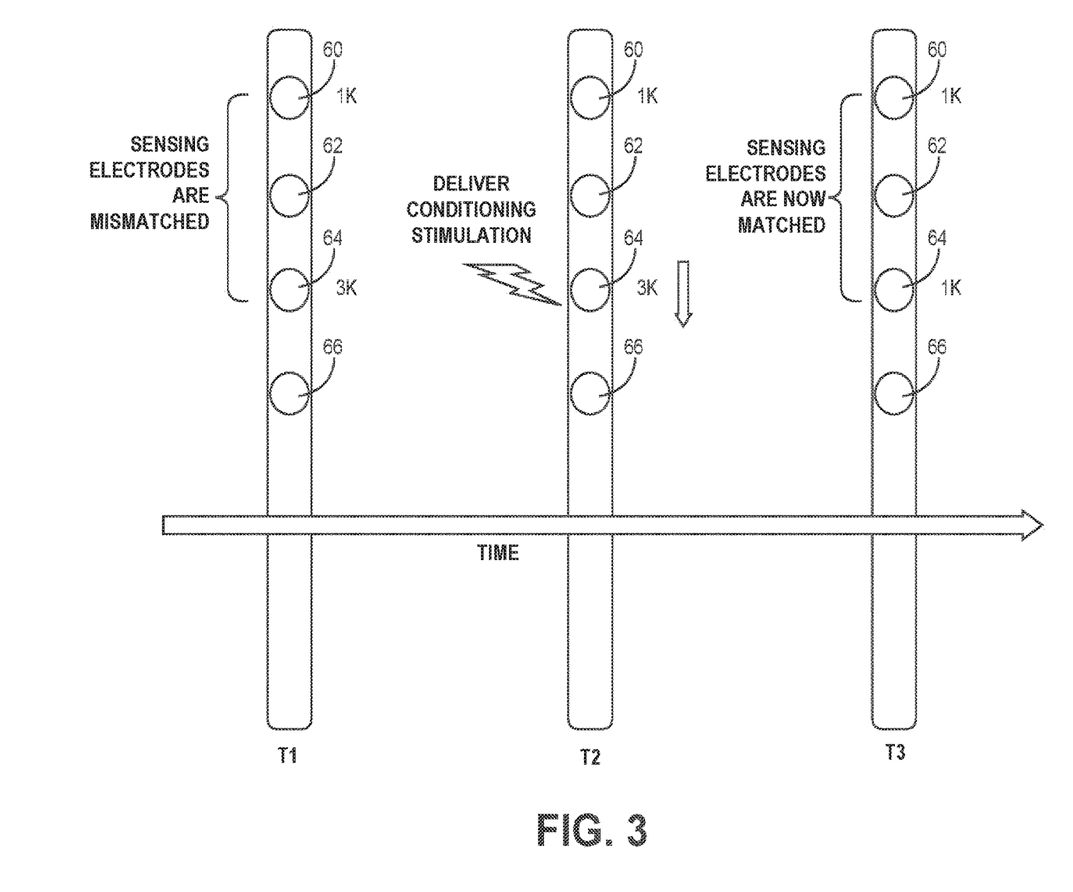
FIG. 3 is a diagram illustrating impedance changes in an exemplary sense electrode combination over time.

FIG. 3 is a diagram illustrating impedance changes in an exemplary sense electrode combination over time. In the illustrated embodiment of FIG. 3, a sense electrode combination 60, 64 are illustrated as having impedances of 1 kΩ and 3 kΩ, respectively, at a time T1. In an exemplary configuration, the electrodes 60, 64 in the sense electrode combination surround a stimulation electrode 62, which can be a unipolar stimulation electrode, or a part of a bipolar or multipolar stimulation electrode combination (e.g., 62, 66). At a time T2, a conditioning stimulation signal is applied to electrode 64 in the sense electrode combination. As described above, in some examples, such a conditioning pulse can be applied to the electrode in the electrode of the sense electrode combination having the highest impedance. Finally, at a time T3, the impedance of electrode 64 has been reduced to 1 kΩ by the conditioning pulse. Accordingly, at time T3, electrodes 60, 64 of the sense electrode combination have matching impedance. In subsequent sensing operation, the CMRR of the sense electrode combination of time T3 will be larger than that of the CMRR of the combination at times T1 or T2, thereby allowing for an increased gain in the signal chain to view signals of interest while reducing the risk of saturation due to a signal at the stimulation electrode 62.

Figure 4:
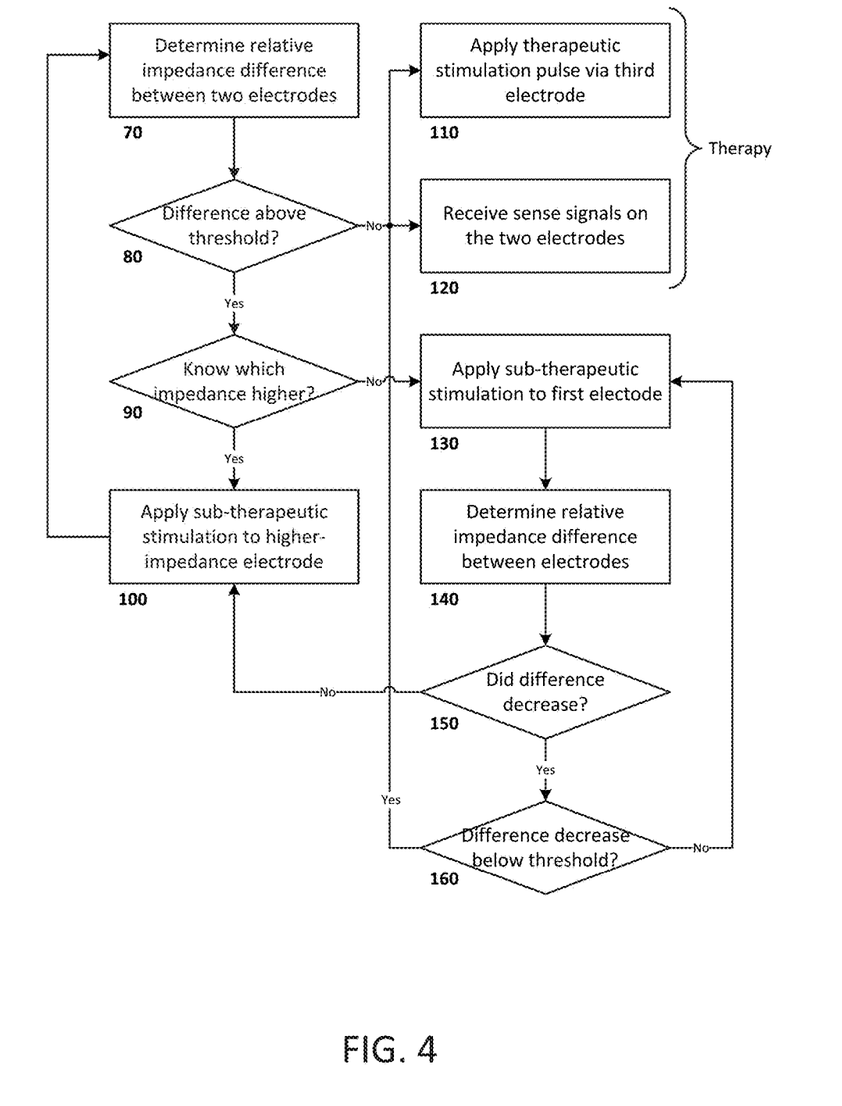
FIG. 4 is a flow diagram illustrating exemplary operation of the system.

FIG. 4 is a flow diagram illustrating exemplary operation of the system. The system can determine the relative impedance difference between two electrodes (70). Such electrodes can include, for example, a sense electrode combination. The system can determine if the relative impedance difference is above a predetermined threshold (80). If so, the system can determine if it is known which electrode has the higher impedance (90). If so, the system can apply a sub-therapeutic stimulation to the higher-impedance electrode (100) to reduce its impedance. After applying the sub-therapeutic stimulation, the system can once again determine the relative impedance difference between the two electrodes (70).

If, on the other hand, it is not known which electrode impedance is the higher of the two, the system can apply a sub-therapeutic stimulation to a first of the two electrodes (130), determine the relative impedance difference between the two electrodes (140), and determine whether or not the impedance difference decreased (150). If the difference did not decrease, then the system can determine that the other electrode is the electrode having the higher impedance, and can subsequently apply sub-therapeutic stimulation to the higher-impedance electrode (100). If the difference did decrease, the system can determine if the impedance difference decreased below a threshold (160). If not, the system continues to apply the sub-therapeutic stimulation to the first electrode (130).

However, if the impedance did decrease below the threshold (160), or if the difference is not above the threshold (80) after determining the relative impedance difference (70), the system can simultaneously apply a therapeutic simulation pulse via a third electrode (110) and receive sense signals on the two electrodes (120). As previously discussed, when the relative impedance difference between the electrodes is below a predetermined threshold, or, in the extreme case, when the relative impedance difference is zero, such as illustrated at time T3 in FIG. 3, the CMRR of the electrodes is more likely to be sufficiently high to reject stimulation pulses (e.g., from the third electrode) and allow for the amplification of received sense signals without saturating the signal chain.

It will be appreciated that, with respect to the flow diagram of FIG. 4, various steps of the process can be performed simultaneously, permuted, or omitted without departing from the scope of the invention. For example, in some embodiments, the system can perform the steps of applying a sub-therapeutic stimulation to a higher-impedance electrode (100), determining the relative impedance difference between the two electrodes (70), and comparing the difference to a threshold (80) substantially simultaneously. In some embodiments, as described elsewhere herein, the system need not determine the relative impedance difference (70) prior to applying a sub-therapeutic stimulation pulse to attempt to improve the CMRR of an electrode combination. Additionally or alternatively, in some examples, the system does not apply therapeutic stimulation pulses (110) at all, but rather is used as a monitoring or diagnostic system.

It will also be appreciated that various steps in the method of FIG. 4 can be performed automatically by the system (e.g., driven by processor 40 of IMD 16), or can be performed manually by a system operator, such as a patient or clinician, for example via programmer 14. In still further embodiments, the system can prompt a system operator to perform one or more steps of the method.

In some situations, sub-therapeutic electrode conditioning procedures can only adjust the impedance of an electrode so much. Accordingly, there could be circumstances in which the relative impedance difference between electrodes in a sense electrode combination cannot be reduced below a threshold, making it difficult to simultaneously amplify signals of interest in the sense signals for analysis without experiencing saturation. In some such embodiments, a decision is made between maintaining the at least one stimulation electrode for the efficacy of the patient, maintaining a sense electrode combination proximate the at least one stimulation electrode for effective monitoring of the affected portions of the patient's brain, and modifying either the stimulation or the sense electrodes in an effort to amplify the received sense signals with reduced risk of saturation.

For example, if alternative stimulation electrodes are available having similar efficacy as an original stimulation electrode, the alternative stimulation electrode can be used in response to the system being unable to adjust the relative impedance difference between an original sense electrode combination associated with the original stimulation electrode below a threshold. An alternative sense electrode combination proximate the alternative stimulation electrode can be conditioned so that the relative impedance difference between the electrodes in the alternative sense electrode combination is below the threshold. In some embodiments, the system can determine the relative impedance difference between a variety of sense electrode combinations. Such impedance information can be used with stimulation electrode efficacy data to make an informed decision for which electrodes are used for stimulation and for sense electrodes. Such decisions can be performed manually by a system operator, or can be automated, for example, based on one or more programs 54 or operating instructions 58 stored in memory 42.

Various examples of the disclosure have been described. While many described embodiments included system for stimulating and sensing from a patient's brain tissue, these are not intended to limit the scope of the invention. For instance, the foregoing techniques can be used in system for only sensing, such as purely diagnostic system. Additionally or alternatively, systems can be used in other physiological sensing applications, such as neural tissue outside of the brain, muscle tissue, etc. These and other examples are within the scope of the following claims.

The invention claimed is:

1. A system comprising:
a first electrode and a second electrode, the first electrode and the second electrode configured to electrically and chronically engage neural tissue of a patient, wherein neural tissue is brain tissue or spinal cord tissue; and
a processor in communication with the first electrode and the second electrode, the processor configured to:
receive electrical signals representative of a patients physiological activity;
determine a first relative impedance difference between the first electrode and the second electrode, wherein an impedance of the first electrode is greater than an impedance of the second electrode;
cause the impedance of the first electrode to decrease by controlling a stimulation generator to provide a first impedance-reducing stimulation pulse from the first electrode based on the determined relative impedance difference, such that the first relative impedance difference between the first electrode and the second electrode is reduced, wherein the impedance-reducing pulse comprises pulse characteristics configured to reduce a localized electrode-to-neural tissue impedance, wherein an extent of the localized electrode-to-neural tissue impedance reduction effect is less than a distance between the first electrode and a nearest adjacent electrode;
determine a second relative impedance difference between the first electrode and the second electrode;
in response to the second relative impedance difference exceeding a predetermined threshold, cause the impedance of the first electrode to decrease by controlling the stimulation generator to provide a second impedance-reducing stimulation pulse from the first electrode based on the determined relative impedance difference, such that the second relative impedance difference between the first electrode and the second electrode is reduced;
determine a third relative impedance difference between the first electrode and the second electrode; and
in response to the third relative impedance difference satisfying the predetermined threshold, receive subsequent electrical signals with the first electrode and the second electrode having the reduced relative impedance difference.

2. The system of claim 1, further comprising a third electrode in communication with the processor, the third electrode being separate from first electrode and the second electrode and being configured to electrically engage the neural tissue of the patient.

3. The system of claim 2, wherein the processor is further configured to control the stimulation generator to provide a therapeutic treatment stimulation pulse from the third electrode while the processor is simultaneously configured to detect signals from the patient via the first electrode and the second electrode.

4. The system of claim 3, wherein the first electrode, the second electrode, and the third electrode are selectable from a plurality of electrodes.

5. The system of claim 2, wherein the processor is configured to:
control the stimulation generator to provide a test stimulation pulse from the third electrode;
receive signals from the first electrode and the second electrode indicative of the patient's physiological activity; and
determine the common-mode rejection ratio (CMRR) between the first electrode and the second electrode based on the received signals.

6. The system of claim 5, wherein the determined CMRR is indicative of the relative impedance difference between the first electrode and the second electrode.

7. The system of claim 5, wherein the processor is configured to, in the event that the determined CMRR is above a predetermined threshold, control the stimulation generator to provide the impedance-reducing stimulation pulse.

8. The system of claim 4, wherein the processor and the plurality of electrodes are implantable within the patient.

9. The system of claim 8, further comprising a user interface by which a user can manually query the system to determine the relative impedance difference between the first electrode and the second electrode and manually instruct the system to provide the first impedance-reducing stimulation pulse from the first electrode.

10. The system of claim 1, wherein the processor is configured to periodically determine the relative impedance difference between the first electrode and the second electrode, and, in the event that the relative impedance difference exceeds a predetermined threshold, provide the first impedance-reducing stimulation pulse from the first electrode.

11. The system of claim 1, wherein the processor is configured to monitor the relative impedance difference between the first electrode and the second electrode while controlling the stimulation generator to provide the first impedance-reducing stimulation pulse and the second impedance-reducing stimulation pulse from the first electrode.

12. The system of claim 11, wherein to monitor the relative impedance difference between the first electrode and the second electrode while controlling the stimulation generator to provide the first impedance-reducing stimulation pulse and the second impedance-reducing stimulation pulse from the first electrode comprises:
periodically ceasing controlling the stimulation generator to provide the first impedance-reducing stimulation pulse or the second impedance-reducing stimulation pulse,
determining the relative impedance difference, and,
in response to the relative impedance difference being above a predetermined threshold, resuming the controlling the stimulation generator to provide the first impedance-reducing stimulation pulse or the second impedance-reducing stimulation pulse.

13. The system of claim 1, wherein the processor is configured to determine the relative impedance difference between the first electrode and the second electrode based on a result of signals received from the first electrode and the second electrode.

14. The system of claim 1, wherein the processor is configured to control the stimulation generator to provide a plurality of stimulation pulses to at least one of the first electrode and the second electrode.

15. The system of claim 1, wherein the first impedance-reducing stimulation pulse and the second impedance-reducing stimulation pulse has at least one non-therapeutic characteristic.

16. The system of claim 1 wherein the received electrical signals are generated from local field potentials (LFP) within the neural tissue.

* * * * *